United States Patent [19]
Elokdah et al.

[11] Patent Number: 5,783,707
[45] Date of Patent: Jul. 21, 1998

[54] 2-THIOXO-IMIDAZOLIDIN-4-ONE DERIVATIVES

[75] Inventors: Hassan M. Elokdah, Yardley, Pa.; Sie-Yearl Chai, Lawrenceville, N.J.; Theodore S. Sulkowski, Wayne; Donald P. Strike, St. Davids, both of Pa.

[73] Assignee: American Home Products Corporation, Madison, N.J.

[21] Appl. No.: 754,440

[22] Filed: Nov. 21, 1996

Related U.S. Application Data

[60] Provisional application No. 60/007,661 Nov. 28, 1995.

[51] Int. Cl.$^6$ .................................................. C07D 233/86
[52] U.S. Cl. .................................... 548/321.1; 548/317.1; 548/319.1; 548/320.5
[58] Field of Search ......................... 548/317.1, 319.1, 548/320.5, 321.1

[56] References Cited

U.S. PATENT DOCUMENTS

| | | |
|---|---|---|
| 2,551,134 | 5/1951 | Jennings et al. |
| 2,649,459 | 8/1953 | Brooker et al. |
| 3,134,663 | 5/1964 | Kroll |
| 3,923,994 | 12/1975 | Magnani |
| 4,473,393 | 9/1984 | Nagpal |
| 4,749,403 | 6/1988 | Liebl et al. |
| 5,137,904 | 8/1992 | Baran et al. |
| 5,411,981 | 5/1995 | Gaillard-Kelly et al. |

FOREIGN PATENT DOCUMENTS

| | | |
|---|---|---|
| 578516 | 1/1994 | European Pat. Off. |
| 584694 | 3/1994 | European Pat. Off. |
| 87030 | 11/1973 | Japan |
| 297461 | 9/1992 | Japan |
| 9318057 | 9/1993 | WIPO |
| 9420460 | 9/1994 | WIPO |

OTHER PUBLICATIONS

Tanaka et al., "Photographic Spectral Sensitizers" CA 112:79441, 1990.
Okazaki et al, "Silver Halide Photographic Emulsions" CA 105:105695, 1986.
Arenal et al, "Methyl Derivatives of 2–thiohydantoin" CA 102:131962, 1985.
Mitsubishi, "Spectrally Sensitized Silver, etc. " CA 95:123986, 1981.
Lyubich, et al. "Study of Polymerocyanines. V., etc" CA 88:8482, 1978.
Gerbal, "Methine Dyes as Sensitizers, etc" CA 79:67829, 1973.
Cogrossi, "Infrared Spectra of Some 1,3–dihetera, etc" CA 77:26890, 1972.
Poppe et al, "Photographic Sensitizing Dyes", CA 65: 9072g, 1966.
Badimon et al., "High Density Lipoprotein Plasma Fraction Inhibit Aortic Fatty Streaks in Cholesterol–Fed Rabbits", Lab. Invest., 60 (1989) 455–461.
Barr et al., "Protein–lipid Relationships in Human Plasma", Am. J. Med. 11 (1951) 480–493.
Glass et al., "Tissue Sites of Degradation of High Density Lipoprotein apo A–1 in the Rat", Circulation 66 (Suppl. II (1982) 102.
Glomset, "The plasma lecithin:cholesterol acyltransferase reaction", J. Lipid Research, 9 (1968) 155–167.
Gofman et al., "Ischemic Heart Disease, Atherosclerosis and Longevity", Circulation 34 (1966) 679–697.
Gordon et al., "High–Denisty Lipoprotein Cholesterol and Cardiovascular Disease", Circulation 79 (1989) 8–15.
Grow and Fried, "Interchange of Apoprotein Components between the Human Plasma High Density Lipoprotein Subclasses $HDL_2$ and $HDL_3$ in Vitro", J. Biol. Chem. 253 (1978 (8034–8041.
Lagocki and Scanu, "In Vitro Modulation of the Apolipoprotein Composition of High Denisity Lipoprotein", J. Biol. Chem. 255 (1980) 3701–3706.
MacKinnon et al., "Metabolism of High Density Lipoproteins by the Perfused Rabbit Liver", J. Biol. Chem. 261 (1986) 2548–2552.
Miller and Miller, "Plasma–High–Density–Lipoprotein Concentration and Development of Ischemic Heart Disease", Lancet 1 (1975) 16–19.
Miller et al., "Relation of angiographically defined coronary artery disease to plasma lipoprotein subfractions and apolipoproteins", Br. Med. J. 282 (1981) 1741–1744.
Picardo et al., "Partially Reassembled High Density Lipoproteins", Arteriosclerosis 6 (1986) 434–441.
Schaefer et al., "Transfer of human lymph chylomicron constituents to other lipoprotein density fractions during in vitro lipolysis", J. Lipid Res. 23 (1982) 1259–1273.
Stampfer et al., "A Prospective Study of Cholesterol, Apolipoproteins, and the Risk of Myocardial Infarction", N. Eng. J. Med. 325 (1991) 373–381.

Primary Examiner—Patricia L. Morris
Attorney, Agent, or Firm—Rebecca R. Barrett

[57] ABSTRACT

The compound of formula I

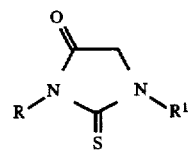

in which $R^1$ is alkyl; and R is alkyl, naphthyl, benzhydryl, fluorophenylmethyl, phenethyl, 1-(fluorophenyl)ethyl, 5-chloro-2-methoxyphenyl, trifluoromethoxyphenyl, trifluoromethylphenyl, methylsulfanylphenyl or pyridyl are useful for increasing blood serum HDL levels.

10 Claims, No Drawings

2-THIOXO-IMIDAZOLIDIN-4-ONE DERIVATIVES

This application claims the benefit of U.S. application Ser. No. 60/007,661, filed Nov. 28, 1995.

BACKGROUND OF INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al. *Am. J. Med.*, 11 (1951) 480–493; Gofman et al. *Circulation*, 34 (1966) 679–697; Miller and Miller, *Lancet*, 1 (1975) 16–19; Gordon et al. *Circulation*, 79 (1989) 8–15; Stampfer et al. *N. Engl. J. Med.*, 325 (1991) 373–381; Badimon et al. *Lab. Invest.*, 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles appears to be correlated with a decrease in the number of sites of stenosis in the coronary arteries of humans (Miller et al. *Br. Med. J.*, 282 (1981) 1741–1744).

There are several mechanisms by which HDL may protect against the progression of atherosclerosis. Studies in vitro have shown that HDL is capable of removing cholesterol from cells (Picardo et al. *Arteriosclerosis*, 6 (1986) 434–441). Data of this nature suggests that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al. *Circulation*, 66 (*Suppl.* 1) (1982) 102; MacKinnon et al. *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.*, 253 (1978) 1834–1841; Lagocki and Scanu, *J. Biol. Chem.*, 255 (1980) 3701–3706; Schaefer et al. *J. Lipid Res.*, 23 (1982) 1259–1273). Accordingly, agents which increase HDL cholesterol concentrations are useful as anti-atherosclerotic agents, particularly in the treatment of dys-lipoproteinemias and coronary heart disease.

U.S. Pat. No. 5,137,904 discloses a group of thiohydantoin derivatives of the formula

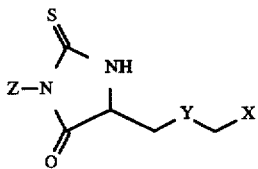

in which Z is alkyl, phenylalkyl, phenyl or substituted phenyl, where the substituent is a halogen, alkyl, alkoxy or halogenated alkyl group; X is phenyl, halophenyl, alkyl, alkenyl, or alkynyl; and Y is S or O. These compounds inhibit collagen-induced and ADP-induced platelet aggregation.

EP 0584694 and WO 93/18057 disclose a group of imidazolidin-3-yl benzoyl or alkanoyl amino acid derivatives as inhibitors of cell-cell adhesion for use in inhibition of thrombocyte aggregation, metastasis and osteoclast formation. Chronic administration for prevention of arteriosclerosis and thrombosis is disclosed.

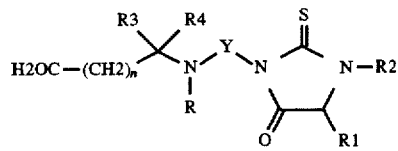

in which Y=—(CH$_2$)$_n$—CO— or —Ph—CO—.

JP 04,297,461 discloses a group of 2-thiohydantoin compounds of the following formula, said to be useful as anti-bacterial, anti-viral, anti-inflammatory and anti-rheumatic agents:

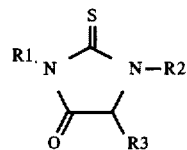

where R$^1$ is lower alkyl, lower alkenyl, phenyl(lower)alkyl or substituted phenyl with 1-3 groups chosen from lower alkyl, lower alkoxy, halogen, lower alkoxycarbonyl or hydroxy;

R$^2$ is either hydrogen or alkanoyl; and

R$^3$ is hydrogen, lower alkyl, phenyl, phenyl (lower) alkyl, or a lower alkylthio, lower alkyl group that can be substituted with one to three phenyl groups that have had a lower alkoxy group.

EP 0578516 discloses a group of 2-thiohydantoins, said to be useful anti-androgenic agents for treatment of various cancer, of the formula:

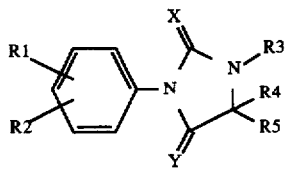

where

X is oxygen or sulfur;

Y is oxygen, sulfur or NH

R$^1$ and R$^2$ are cyano, nitro, halogen, trifluoromethyl, or a free or esterified carboxylic acid or salt;

R$^3$ is hydrogen, alkyl, alkenyl, alkynyl, aryl or aryl-alkyl;

R$^4$ and R$^5$ are hydrogen, optionally substituted alkyl, or cycloalkyl.

U.S. Pat. No. 5,411,981 discloses compounds closely related to EP 0578516, supra, where R$^4$ and R$^5$ are both methyl.

U.S. Pat. No. 3,923,994 discloses a group of 3-aryl-2-thiohydantoin derivatives of the following formula, which have anti-arthritic activity:

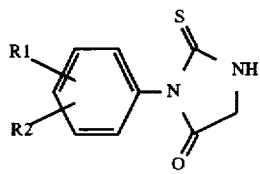

where $R^1$ and $R^2$ are hydrogen, chloro, bromo, fluoro or alkyl of 1–2 carbon atoms.

JP 73 87,030 discloses a group of 3-phenyl-2-thiohydantoin derivatives useful as herbicides.

U.S. Pat. No. 4,473,393 discloses a group of pesticidal thiohydantoin compositions.

DESCRIPTION OF INVENTION

In accordance with this invention there is provided a group of substituted 2-thioxo-imidazolidin-4-one derivatives that are useful for increasing HDL cholesterol concentration in the blood of a mammal. These substituted 2-thioxo-imidazolidin-4-one derivatives are depicted by structural formula I:

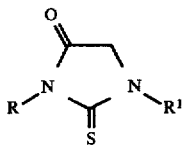

in which $R^1$ is alkyl of 1 to 6 carbon atoms; and

R is alkyl of 1 to 6 carbon atoms, naphthyl, benzhydryl, fluorophenylmethyl, phenethyl, 1-(fluorophenyl)ethyl, 5-chloro-2-methoxyphenyl, trifluoromethoxyphenyl, trifluoromethylphenyl, methylsulfanylphenyl or pyridyl.

Of these compounds, the preferred members are those in which $R^1$ is alkyl of 1 to 3 carbon atoms; and R is alkyl of 1 to 4 carbon atoms, 2-naphthyl, benzhydryl, 4-fluorophenylmethyl, phenethyl, 1-(4-fluorophenyl)ethyl, 5-chloro-2-methoxyphenyl, 4-trifluoromethoxyphenyl, 2-trifluoromethylphenyl, 2-methylsulfanylphenyl or 3-pyridyl.

The compounds of the invention can be prepared readily according to the following reaction scheme or modification thereof using readily available starting materials, reagents and conventional synthetic procedures. It is also possible to make use of variants of these process steps, which in themselves are known to and well within the preparatory skill of the medicinal chemist. In the following reaction scheme, $R^2$ is hydrogen or alkyl of 1 to 6 carbon atoms and X is a halogen.

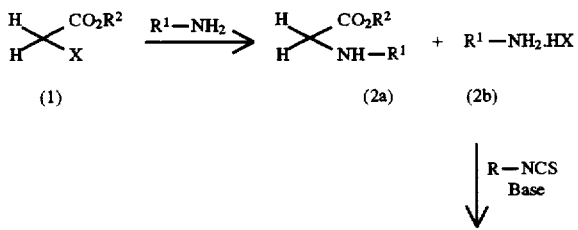

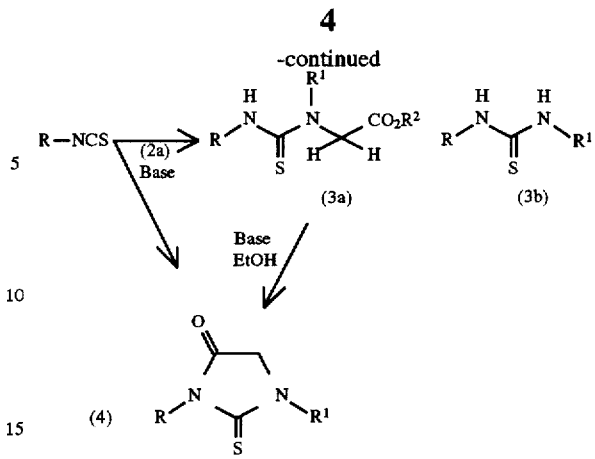

N-Substituted amino acids (2a) were prepared by reacting the corresponding a-halo acids (1) with the appropriate amines (excess). The reaction was carried out either neat or in water at ambient temperature for 18 hours. One equivalent of the amine scavenges the hydrohalide formed during the alkylation forming the amine hydrohalide (2b) as a side product. The N-alkyl amino acids (2a) were either purified by crystallization from an appropriate solvent, or reacted with the isothiocyanates as crude product mixtures containing the amine hydrohalide salt. Reaction of 2a with isothiocyanates is carried out in chloroform or methylene chloride in the presence of a base such as triethyl amine. The mixture is heated at reflux for 3 to 18 hours. The reaction affords either the thiourea (3a) or the thiohydantoin (4) directly (depending on the nature of $R^1$). Cyclization of 3a to the thiohydantoin (4) is accomplished by refluxing in ethanol for 2 to 3 hours in the presence of base (triethyl amine). In the case of reacting the crude product mixture (2a & 2b) with isothiocyanates, the thiourea (3b) is formed as a side product along with 4. Purification of 4 was achieved by 1) fractional crystallization, 2) flash chromatography, 3) extracting 3b in 2N hydrochloric acid or 4) precipitating 3b as its hydrochloride salt from an appropriate solvent such as ethyl acetate or diethyl ether.

This invention also provides pharmaceutical compositions comprised of the 2-thioxo imidazolidin-4-one derivatives either alone or in combination with excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 10 to about 200 milligrams/kilogram per day. However, in general, satisfactory results are indicated to be obtained at daily dosages in the range of from 400 milligrams to about 2000 milligrams, conveniently administered in divided doses two to four times a day.

The ability of the compounds of this invention to increase blood serum HDL levels was established by the following standard experimental procedure for determination of HDL cholesterol:

Male Sprague-Dawley rats weighing 200-225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005-0.1% of the total diet. Body weight and food consumption are recorded prior to diet administration and at termination. Typical doses of the test substances are 5-100 mg/kg/day.

At termination, blood is collected from anesthetized rats and the serum is separated by centrifugation. Total serum cholesterol is assayed using the Sigma Diagnostics enzymatic kit for the determination of cholesterol, Sigma Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 ul of serum is injected onto Superose 12 and Superose 6 (Pharmacia), in series, with a column buffer of 0.05M Tris (2-amino-2-hydroxymethyl-1,3-propanediol) and 0.15M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration, in serum, is calculated as the percent of total cholesterol as determined by FPLC multiplied by the total serum cholesterol concentration.

Test compounds were administered at a dose of 100 mg/kg. The duration of treatment was eight days. The compounds of the present invention increase HDL cholesterol concentrations as summarized in Table I:

TABLE I

| Compound of Example | HDL Cholesterol Level Increase (%) |
|---|---|
| 1 | 57 |
| 2 | 29 |
| 3 | 39 |
| 4 | 39 |
| 5 | 265 |
| 6 | 26 |
| 7 | 95 |
| 8 | 65 |
| 9 | 115 |
| 10 | 49 |
| 11 | 30 |
| 12 | 62 |

The following examples are presented to illustrate the production of representative compounds useful in the method of this invention, rather than as a limit to the scope of applicant's invention:

EXAMPLE 1

3-Benzhydryl-1-methyl-2-thioxo-imidazolidin-4-one

A mixture of sarcosine ethyl ester hydrochloride (7.68 g), benzhydryl-isothiocyanate (11.25 g), triethyl amine (12 g) and chloroform (200 mL) was heated at reflux for 5 hours. The mixture was cooled to ambient temperature, washed with 1N HCl (2×200 mL), then with water (200 mL) The organic phase was evaporated to dryness. The residue was crystallized from ethanol to give the title compound (7.40 g) as an off-white solid, m.p. 139°–141° C. Anal. Calcd. for $C_{17} H_{16} N_2 O S$: C, 68.89; H, 5.44; N, 9.45. Found: C, 68.92; H, 5.43; N, 9.58. Mass spectrum (EI, M.$^+$) m/z 296.

EXAMPLE 2

1-Methyl-3-(pyridin-3-yl)-2-thioxo-imidazolidin-4-one

A mixture of sarcosine ethyl ester hydrochloride (7.68 g), pyridin-3-yl-isothiocyanate (6.8 g), triethyl amine (10.1 g) and chloroform (200 mL) was heated at reflux for 3.5 hours. The solvent was evaporated. The residue was dissolved in ethyl acetate (300 mL) and washed with water (2×200 mL). The organic phase was dried over anhydrous magnesium sulfate. The solvent was evaporated. Crystallization from ethyl acetate afforded the title compound (4.1 g) as an off-white solid, m.p. 149°–151°C. Anal. Calcd. for $C_9 H_9 N_3 O S$: C, 52.16; H, 4.38; N, 20.28. Found: C, 52.16; H, 4.05; N, 20.06. Mass spectrum (EI, M.$^+$) m/z 207.

EXAMPLE 3

3-(5-Chloro-2-methoxyphenyl)-1-methyl-2-thioxo-imidazolidin-4-one

A mixture of sarcosine ethyl ester hydrochloride (7.68 g), 5-chloro-2-methoxyphenyl-isothiocyanate (10.0 g), triethyl amine (10.0 g) and chloroform (150 mL) was heated at reflux for 4.5 hours. The mixture was cooled to ambient temperature. The precipitated solid was collected, washed with chloroform and air dried to give the title compound (11.8 g) as an off-white solid, m.p. 245°–247° C. Anal. Calcd. for $C_{11} H_{11} Cl N_2 O_2 S$: C, 48.80; H, 4.10; N, 10.35. Found: C, 48.42; H, 3.96; N, 10.33. Mass spectrum (EI, M.$^+$) m/z 270.

EXAMPLE 4

3-(5-Chloro-2-methoxyphenyl)-1-ethyl-2-thioxo-imidazolidin-4-one

2-Chloro acetic acid (27.5 g) was added portionwise while stirring to a 70% aqueous ethyl amine solution (500 mL). The addition was carried over a period of 30 minutes. The mixture was stirred at ambient temperature for 18 hours. The mixture was then evaporated to a viscous oily residue (55 g). The crude product consisted of a 1:1 mixture of N-ethyl glycine and ethyl amine hydrochloride. This product mixture was used without further purification.

A mixture N-ethyl glycine (9.2 g), 5-chloro-2-methoxyphenyl-isothiocyanate (10 g), triethylamine (10.1 g), methylene chloride (150 mL) was heated at reflux for 3.5 hours. The mixture was evaporated to dryness. The residue collected, washed with hot ethanol and dried. Title compound (7.6 g) was obtained as a creamy solid, m.p. 171°–174° C. Anal. Calcd. for $C_{12} H_{13} Cl N_2 O_2 S$: C, 50.61; H, 4.60; N, 9.84. Found: C, 50.33; H, 4.50; N, 9.69. Mass spectrum (EI, M.$^+$) m/z 284/286.

EXAMPLE 5

1-Ethyl-2-thioxo-3-(4-trifluoromethoxyphenyl)-imidazolidin-4-one

The title compound was prepared by the procedure described in Example 4 using 9.2 g of N-ethyl glycine, 10.9 g of 4-trifluoromethoxyphenyl-isothiocyanate, 10.1 g of triethylamine, and 150 mL of methylene chloride. Purification was achieved by flash chromatography on silica gel (methylene chloride). Title compound (4.6 g) was obtained as a creamy solid, m.p. 116°–119° C. Anal. Calcd. for. $C_{12} H_{11} F_3 N_2 O_2 S$: C, 47.37; H, 3.64; N, 9.21. Found: C, 47.20; H, 3.50; N, 9.13. Mass spectrum (EI, M.$^+$) m/z 304.

EXAMPLE 6

1-Ethyl-3-(4-fluorobenzyl)-2-thioxo-imidazolidin-4-one

The title compound was prepared by the procedure described in Example 4 using 9.2 g of N-ethyl glycine, 8.4 g of 4-fluorobenzyl-isothiocyanate, 10.1 g of triethylamine, and 150 mL of methylene chloride. Purification was achieved through crystallization from ethyl acetate/hexane mixture. Title compound (4.85 g) was obtained as a white solid, m.p. 73°–76° C. Anal. Calcd. for. $C_{12} H_{13} F N_2 O S$: C, 57.12; H, 5.19; N, 11.10 Found: C, 56.97; H.5.15; N, 11.06. Mass spectrum (EI, M.$^+$) m/z 252.

EXAMPLE 7

1-Ethyl-3-isobutyl-2-thioxo-imidazolidin-4-one

The title compound was prepared by the procedure described in Example 4 using 9.2 g of N-ethyl glycine, 5.7 g of isobutyl-isothiocyanate, 10.1 g of triethylamine, and 150 mL of methylene chloride. Purification was achieved by flash chromatography on silica gel (methylene chloride). Title compound (2.3 g) was obtained as an oil. Anal. Calcd. for. $C_9 H_{16} N_2 O S$: C, 53.97; H, 8.05; N, 13.99. Found: C, 54.01; H, 8.21; N, 14.00. Mass spectrum (EI, M.$^+$) m/z 200.

EXAMPLE 8

1-Ethyl-3-(naphthalen-2-yl)-2-thioxo-imidazolidin-4-one

The tide compound was prepared by the procedure described in Example 4 using 9.2 g of N-ethyl glycine, 9.3 g of 2-naphthyl-isothiocyanate, 10.1 g of triethylamine, and 150 mL of methylene chloride. Purification was achieved through crystallization from ethanol. Title compound (4.7 g) was obtained as a light pink solid, m.p. 156°–159° C. Anal. Calcd. for. $C_{15} H_{14} N_2 O S$: C, 66.64; H, 5.22; N, 10.36 Found: C, 66.69; H,5.24; N, 10.42. Mass spectrum (EI, M.$^+$) m/z 270.

EXAMPLE 9

1-Ethyl-2-thioxo-3-(2-trifluoromethylphenyl)-imidazolidin-4-one

The tide compound was prepared by the procedure described in Example 4 using 9.2 g of N-ethyl glycine, 10.2 g of 2-(trifluoromethyl)-phenyl-isothiocyanate, 10.1 g of triethylamine, and 150 mL of methylene chloride. The residue was further purified by flash chromatography on silica gel (methylene chloride). Crystallization from ethanol afforded the title compound (2.7 g), m.p. 82°–85° C. Anal. Calcd. for. $C_{12}H_{11}F_3N_2OS$: C, 50.00; H, 3.85; N,9.72. Found: C, 50.00; H, 3.61; N, 9.61. Mass spectrum (EI, M.⁺) m/z 288.

EXAMPLE 10

1-Ethyl-3-[1-(4-fluorophenyl)-ethyl]-2-thioxo-imidazolidin-4-one

A mixture of the crude N-ethyl glycine (18.4 g), 1-(4-fluorophenyl)-ethyl-isothiocyanate (18.1 g), triethyl amine (20.2 g) and chloroform (300 mL) was heated at reflux for 18 hours. The solvent was evaporated. The residue was dissolved in ethyl acetate (400 mL) and water (300 mL). The organic phase was washed with 1N HCl (2×300 mL), then evaporated to dryness. Crystallization from ethyl acetate afforded the title compound (8.8 g) as a light yellow solid, m.p. 93°–95° C. Anal. Calcd. for. $C_{13}H_{15}FN_2OS$: C, 58.63; H, 5.68; N, 10.52. Found: C, 58.69; H, 5.64; N, 10.58. Mass spectrum (EI, M.⁺) m/z 266.

EXAMPLE 11

1-Ethyl-3-phenethyl-2-thioxo-imidazolidin-4-one

A mixture of the crude N-ethyl glycine (18.4 g), phenethyl-isothiocyanate (16.3 g), triethyl amine (20.2 g) and chloroform (300 mL) was heated at reflux for 18 hours. The solvent was evaporated. The residue was dissolved in ethyl acetate (400 mL) and water (300 mL). The organic phase was washed with 1N HCl (2×300 mL), then evaporated to dryness. Purification was achieved by flash chromatography on silica gel (20% ethyl acetate in hexane) The title compound (15.0 g) was obtained as an off-white solid, m.p. 66°–68° C. Anal. Calcd. for. $C_{13}H_{16}N_2OS$: C, 62.87; H, 6.49; N, 11.28. Found: C, 63.03; H, 6.49; N, 11.32. Mass spectrum (EI, M.⁺) m/z 248.

EXAMPLE 12

1-Ethyl-3-(2-methylsulfanylphenyl)-2-thioxo-imidazolidin-4-one

A mixture of N-ethyl glycine (9.23 g), 2-(methylthio)-phenyl-isothiocyanate (9.1 g), triethylamine (10.1 g) and methylene chloride (150 mL) was heated at reflux for 3 hours. The mixture was evaporated to dryness. The residue was recrystallized from ethanol to give the title compound (6.5 g) as a creamy solid, m.p. 128°–131° C. Anal. Calcd. for. $C_{12}H_{14}N_2S_2O$: C, 52.11; H, 5.30; N, 10.52. Found: C, 52.28; H, 5.26; N, 10.54. Mass spectrum (EI, M.⁺) m/z 266.

What is claimed is:

1. A compound of formula I

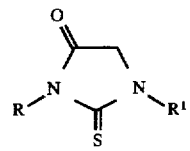

in which

R¹ is alkyl of 1 to 6 carbon atoms; and

R is 1-(fluorophenyl)ethyl, 5-chloro-2-methoxyphenyl, trifluoromethoxyphenyl, trifluoromethylphenyl, or methylsulfanylphenyl.

2. A compound of claim 1 in which R¹ is alkyl of 1 to 6 carbon atoms; and R is benzhydryl, 4-fluorophenylmethyl, 1-(4-fluorophenyl)ethyl, 5-chloro-2-methoxyphenyl, 4-trifluoro-methoxyphenyl, 2-trifluoromethylphenyl, or 2-methylsulfanylphenyl.

3. The compound of claim 1 which is 3-benzhydryl-1-methyl-2-thioxo-imidazolidin-4-one.

4. The compound of claim 1 which is 3-(5-chloro-2-methoxyphenyl)-1-methyl-2-thioxo-imidazolidin-4-one.

5. The compound of claim 1 which is 3-(5-chloro-2-methoxyphenyl)-1-ethyl-2-thioxo-imidazolidin-4-one.

6. The compound of claim 1 which is 1-ethyl-2-thioxo-3-(4-trifluoromethoxyphenyl)-imidazolidin-4-one.

7. The compound of claim 1 which is 1-ethyl-3-(4-fluorobenzyl)-2-thioxo-imidazolidin-4-one.

8. The compound of claim 1 which is 1-ethyl-2thioxo-3-(2-trifluoromethylphenyl)-imidazolidin-4-one.

9. The compound of claim 1 which is 1-ethyl-3-[1-(4-fluorophenyl)-ethyl]-2-thioxo-imidazolidin-4-one.

10. The compound of claim 1 which is 1-ethyl-3-(2-methylsulfanylphenyl)-2-thioxo-imidazolidin-4-one.

* * * * *